United States Patent
Howieson et al.

(10) Patent No.: US 10,224,116 B2
(45) Date of Patent: *Mar. 5, 2019

(54) DISPENSERS AND METHODS OF USE THEREOF

(71) Applicant: eLUCID mHEALTH LIMITED, Manchester (GB)

(72) Inventors: Graham Howieson, Manchester (GB); Farid Khan, Manchester (GB); James Burnstone, Manchester (GB)

(73) Assignee: ELUCID MHEALTH LIMITED, Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/968,185

(22) Filed: May 1, 2018

(65) Prior Publication Data
US 2018/0247704 A1  Aug. 30, 2018

Related U.S. Application Data

(62) Division of application No. 15/519,778, filed as application No. PCT/GB2015/053084 on Oct. 16, 2015, now Pat. No. 9,984,213.

(30) Foreign Application Priority Data

Oct. 16, 2014 (GB) .................................. 1418350.3
Dec. 9, 2014 (GB) .................................. 1421847.3

(51) Int. Cl.
*G06F 19/00* (2018.01)
*G16H 20/13* (2018.01)
(Continued)

(52) U.S. Cl.
CPC .......... *G16H 20/13* (2018.01); *A61B 5/1172* (2013.01); *A61B 5/1176* (2013.01); *A61J 1/03* (2013.01);
(Continued)

(58) Field of Classification Search
CPC . G06F 19/3462; A61B 5/1172; A61B 5/1176; A61J 7/0076; A61J 2200/30; G07C 9/00103; G07C 9/00111; G07C 2209/64
See application file for complete search history.

(56) References Cited

U.S. PATENT DOCUMENTS

| 6,206,238 | B1 * | 3/2001 | Ophardt | A47K 5/1217 |
| | | | | 222/1 |
| 7,359,765 | B2 * | 4/2008 | Varvarelis | A61J 7/0481 |
| | | | | 700/237 |
| 9,984,213 | B2 * | 5/2018 | Howieson | G06F 19/3462 |
| 2003/0222090 | A1 * | 12/2003 | Abdulhay | G07F 11/10 |
| | | | | 221/3 |
| 2007/0186923 | A1 * | 8/2007 | Poutiatine | A61J 7/0038 |
| | | | | 128/200.14 |
| 2007/0244598 | A1 * | 10/2007 | Shoenfeld | G06F 19/00 |
| | | | | 700/236 |

(Continued)

*Primary Examiner* — Thomas D Alunkal
(74) *Attorney, Agent, or Firm* — Stephen J. Weyer, Esq.; Stites & Harbison, PLLC

(57) ABSTRACT

The present invention relates to a dispenser comprising: a) a reclosable opening on, or for fitment on and/or around an opening of, a container having a cavity for receiving at least one unit of a product to be dispensed; b) a controller adapted for controlling the opening of the reclosable opening; c) a receiver adapted for receiving a user authentication signal; d) a power source for powering the controller and receiver; and wherein the dispenser only permits the opening of the reclosable opening upon the receiver receiving a user authentication signal. The invention also relates to a dispensing system, method of dispensing and a kit of parts including such a dispenser. The inventions are particularly suited for dispensing pharmaceutical products to only the intended recipient and also to ensure compliance with dosage regimes.

20 Claims, 14 Drawing Sheets

(51) Int. Cl.
*G07F 17/00* (2006.01)
*A61J 1/03* (2006.01)
*A61J 7/04* (2006.01)
*A61B 5/1172* (2016.01)
*A61B 5/1171* (2016.01)
*A61J 7/00* (2006.01)
*G07C 9/00* (2006.01)
*G06Q 20/40* (2012.01)

(52) U.S. Cl.
CPC .............. *A61J 7/0076* (2013.01); *A61J 7/04* (2013.01); *A61J 7/0409* (2013.01); *G06F 19/00* (2013.01); *G06F 19/3462* (2013.01); *G06Q 20/4014* (2013.01); *G07C 9/00103* (2013.01); *G07C 9/00111* (2013.01); *G07F 17/0092* (2013.01); *A61J 2200/30* (2013.01); *G07C 2209/64* (2013.01)

(56) References Cited

U.S. PATENT DOCUMENTS

| | | | |
|---|---|---|---|
| 2010/0100237 A1* | 4/2010 | Ratnakar | A61J 7/02 700/232 |
| 2010/0230435 A1* | 9/2010 | Wegelin | A47K 5/1217 222/52 |
| 2013/0110283 A1* | 5/2013 | Baarman | A61J 7/0084 700/236 |
| 2013/0197693 A1* | 8/2013 | Kamen | G06F 19/3418 700/244 |
| 2016/0188840 A1* | 6/2016 | Eramian | G06F 19/3462 700/237 |

* cited by examiner

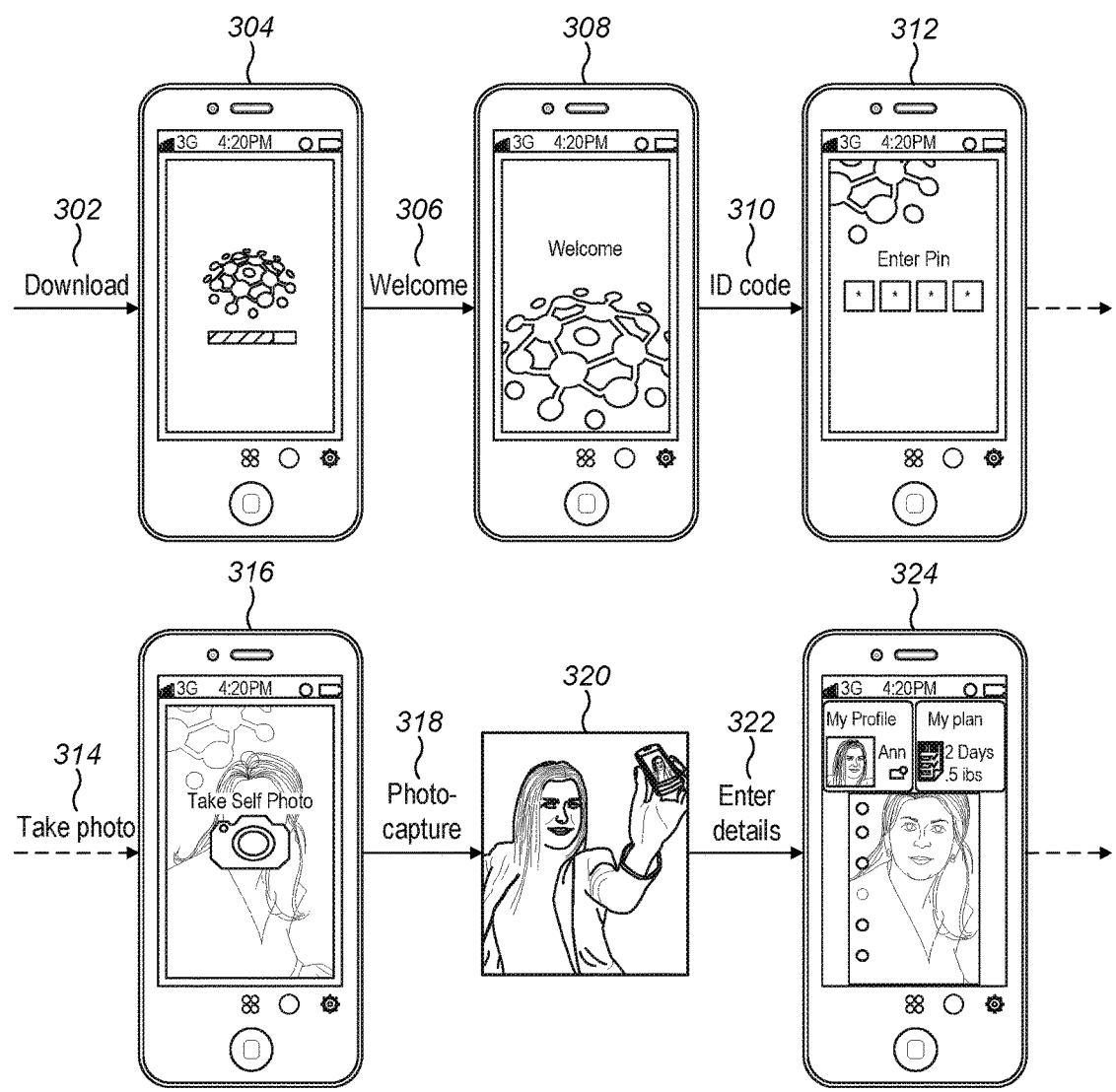

DISPENSERS AND METHODS OF USE THEREOF

CROSS-REFERENCE TO RELATED APPLICATION

This is a divisional of U.S. patent application Ser. No. 15/519,778 filed on Mar. 17, 2017, a 371 application of PCT/GB2015/053084 filed on Oct. 16, 2015, all herein incorporated by reference.

TECHNICAL FIELD OF THE INVENTION

The invention relates to reclosable dispensers and to systems and methods of dispensing (and additionally tracking and recording the dispensing of) products, such as pharmaceuticals, to the intended recipient.

BACKGROUND TO THE INVENTION

Products, such as pharmaceuticals and dietary supplements can be dangerous if incorrectly administered or taken by someone other than the intended recipient (by a child for example). Most medicines need to be administered under a particular regimen to be effective, however, some patients take two does of the medicine if they have missed a previous dose which could be extremely harmful. Lastly, there are issues with patient dose compliance which is often hard to establish by physicians and can lead to further unnecessary treatments or provide incorrect clinical trial data.

A number of devices and systems have been proposed which try and identify compliance issues with patient pharmaceutical administration.

GB2483221 discloses a method of monitoring patient compliance using a camera on a telecommunication device to record the individual pill opening of a blister pack. The automated system detects whether an individual pill seal within the blister pack has been broken using image recognition software. The system collates the data issued by individual telecommunication devices by updating a database and queries it against preset parameters set by the health care professional.

US20140266760 describes a tablet container cap which incorporates sensors, chips, transmitters, and receiver, to record, transmit, and receive data regarding the time intervals between when the container cap was last placed on or taken off of a container. The container cap is for use with pharmaceutical and other health care related vials, bottles and containers. The data transmission is used to monitor a patient's drug administration times and intervals, and allows the patient and/or the patient's caregiver to review the administration data.

US20140297312 discloses computer-based systems and computer-implemented methods for monitoring medication events for an individual.

All of the above systems and methods are aimed at monitoring dose administration. However none of the prior art systems and methods actively prevent administration to anyone other than the patient (or patient carer) or indeed permit stricter compliance with the desired dosage regime. An object of the present invention is to address one or more of the above problems associated with the prior art. It is also an object of the present invention to provide for a dispenser, system or method which prevents administration of a medicine to anyone other than the patient (or patient carer) and optionally only dispenses the medicine in the desired dose within the correct time interval. It is also an object to provide for a dispenser, system or method which actively monitors dose compliance and interacts with a medical records or clinical trial data systems.

SUMMARY OF THE INVENTION

In accordance with a first aspect of the present invention, there is provided a dispenser comprising:
 a. a reclosable opening on, or for fitment on and/or around an opening of, a container having a cavity for receiving at least one unit of a product to be dispensed;
 b. a controller adapted for controlling the opening of the reclosable opening;
 c. a receiver adapted for receiving a user authentication signal;
 d. a power source for powering the controller and receiver; and
 wherein the dispenser only permits the opening of the reclosable opening upon the receiver receiving a user authentication signal.

The receiver may be further adapted for receiving a permitted time interval signal or the permitted time interval has lapsed and the dispenser only permits the opening of the reclosable opening upon additionally receiving a permitted time interval signal or a permitted time interval has lapsed. This can be used to prevent the unit (such as a pharmaceutical) from being dispensed too frequently or not within the desired time window.

The receiver may be further adapted for receiving or assessing whether the user is within a prescribed vicinity of the dispenser and only permits the opening of the reclosable opening upon additionally determining if the user is within the prescribed vicinity. This feature can ensures that the opening of the reclosable opening is only permitted if the user is close by if it is not desired to permit remote opening.

The user authentication signal may be provided by successfully identifying an authorised user by using one or more of the following: facial recognition, finger prints, retina scan, PIN code or password. It will be apparent that a number of other methods of identifying an authorised user may be employed such as voice signatures.

Preferably the user authentication signal is provided upon verifying the user against identification data located on the dispenser or a remote server.

The receiver may be formed as part of a transceiver to enable the dispenser to receive and also submit signals. Such a transceiver may transmit a dispensing signal and/or receipt of an authentication signal to the remote server. This transmission may be via one or more intermediate communication devices.

The authentication signal may be provided by the receiver itself or by a remote device.

A dispensing sensor may be provided which senses when one or more units of product has been advanced towards or through the reclosable opening. The dispensing sensor could comprise a micro-switch arrangement which detects the physical passage of the unit or a light sensor which can detect the optical passage of the unit. The dispensing sensor can be used to provide a dispensing validation signal. The dispensing sensor provides a 'double check' that the unit has indeed been dispensed to prevent false positive dispensing events being logged.

The transceiver may transmit the dispensing signal and/or a dispensing validation signal and/or receipt of an authentication signal to the remote server via the remote device. The device may be configured so that both a dispensing signal and/or a dispensing validation signal are required to confirm that a unit has been dispensed and should the device transmit a dispensing signal without a dispensing validation signal, then an error can be identified by either the remote device or remote server and a remedial course of action permitted.

The remote device will preferably comprise a radio electronic transmitter. A radio electronic transmitter may comprise a range of telecommunication devices, such as a mobile phone. The term "mobile phone", "telecommunication device" and "cell phone" can be used interchangeably and are intended to be used to describe mobile communication devices which are capable of communicating wirelessly with the dispenser and also a remote server if desired.

The term "signal" may encompass a number of different electronic communication signals, such as a radio signal.

The controller may comprise a micro-switch arrangement which controls the opening of the reclosable opening. The controller may comprise a motor which acts to advance one or more units of product towards or through the reclosable opening. Preferably, the units of product are advanced by means of the motor powering a ratchet arrangement, whereby a single unit is advanced towards or through the reclosable opening. Such a ratchet arrangement would prevent further product units advancing towards or through the reclosable opening as the arrangement would essentially be locked until powered by the motor again. Alternatively, the units of product are advanced by means of the motor continually powering a mechanism, which optionally may include gearing, so that the units of product are advanced towards or through the reclosable opening at particular time intervals which correlate to speed of the motor and/or mechanism. Additional mechanical and/or electro-mechanical arrangements for controlling the opening of the reclosable opening will of course be apparent to the skilled addressee.

The dispenser can be used for dispensing a number of different items but it is particularly suited to products comprising pharmaceutical, nutraceutical, nutritional or dietary supplements. The opening of the reclosable opening may permit only a single or metered dose of the product to be dispensed. The product may be in the form of a tablet or capsule. In the alternative, the product may be in the form of a liquid, powder or suspension.

The one or more units of product may be gravity fed to the reclosable opening. Preferably, the dispenser is configured to be stored or held upright so as to enable one or more units of the product to be gravity fed to the reclosable opening. The dispenser may be in the form of a cylindrical housing having a base and a top and where the base is larger than the top. Additionally, the top may be substantially convex and optionally weighted so as to make the dispenser unstable unless it is stored in an upright position resting upon its base.

It will be apparent to the skilled addressee that the dispenser may be retro-fitted to the opening of an existing container, such as a typical medical bottle or metered inhaler.

In accordance with another aspect of the present invention, there is a provided a dispensing system comprising:
  a. a dispenser having a reclosable opening on, or for fitment on and/or around an opening of, a container having a cavity for receiving at least one unit of a product to be dispensed;
  b. an identification device for recognising an authorised user;
  c. a communication arrangement for communicating to the dispenser that recognition of the authorised user has been confirmed by the identification device; and wherein only when the recognition of the authorised user is communicated, does the dispenser permit one or more units of the product to be dispensed through the reclosable opening.

Preferably, only when the recognition of the authorised user is communicated and additionally a permitted time interval signal or the permitted time interval has lapsed and/or the user is within a prescribed vicinity of the dispenser, does the dispenser permit one or more units of the product to be dispensed through the reclosable opening.

The recognition device may use one or more of the following: facial recognition, finger prints, retina scan, PIN code or password. Again it will be apparent to the skilled addressee that other recognition devices may also be employed if desired.

The recognition of the authorised user may be provided upon verifying the user against identification data located on a remote server. The communication arrangement may transmit a dispensing signal and/or a dispensing validation signal and/or recognition of the authorised user to the remote server.

The identification device may comprise a remote device. The communication device may transmit a dispensing signal and/or a dispensing validation signal and/or recognition of the authorised user to the remote server via the remote device. The remote device will preferably comprise a mobile phone.

The product may comprise a pharmaceutical, nutraceutical, nutritional or dietary supplement.

The opening of the reclosable opening may permit a single or metered dose of the product to be dispensed. The product may be in the form of a tablet, liquid, powder or suspension.

In accordance with a yet further aspect of the present invention, there is provided a method of dispensing at least one unit of a product from the cavity of a container to an authorised user comprising:
  a. providing a container having an opening and a cavity for receiving at least one unit of the product to be dispensed and the dispenser having a controllably reclosable opening;
  b. providing an identification device for recognising an authorised user;
  c. providing a communication arrangement for communicating to the dispenser when recognition of the authorised user has been confirmed by the identification device; and
  wherein only when the recognition of the authorised user is communicated to the dispenser, does the dispenser permit one or more units of the product to be dispensed through the reclosable opening.

It is preferred that the method employs a system as herein above described.

In accordance with a yet further aspect of the present invention, there is provided a kit of parts comprising:
  a. a dispenser having a reclosable opening on, or for fitment on and/or around an opening of, a container which incorporates or is operably connected to:
  b. an identification device for recognising an authorised user;
  c. a communication arrangement for communicating to the dispenser that recognition of the authorised user has been confirmed by the identification device so that the reclosable opening can be opened; and
  d. a container having a cavity for receiving at least one unit of a product to be dispensed and an opening.

It is preferred that the kit is used to produce a system as herein above described.

In accordance with yet a further aspect of the present invention, there is provide a dispensing container comprising:
- a) a cavity for receiving at least one unit of product to be dispensed;
- b) a base having an aperture adapted to allow at least one unit of product to be dispensed when desired; and
- c) a dispensing control arrangement for controlling the dispensing of at least one unit of product through the aperture in the base in accordance with a dispensing protocol.

The dispensing container will preferably further comprise:
- d) a cap releasably attached to the base so as to cover the aperture in the base and capable of storing at least one unit of product after it has been dispensed.

Preferably, the dispensing protocol comprises a pre-determined time interval. Such a time interval may be desirable for dispensing certain pharmaceutical products such as drug rehabilitation medicines like methadone. The protocol may be specifically tailored to individual patient requirements or may be defined by the preferred/suggested dosage regime of the product manufacturer or physician.

The dispensing protocol may alternately, or additionally, comprises receiving a user authentication signal from a remote device. Such user authentication signals are described in detail in earlier embodiments. The remote device may be a mobile phone or similar device which is able to verify the identity of the individual wishing to take the product.

The controller may comprise a micro-switch or ratchet arrangement which controls the dispensing of one or more units of product through the aperture. The controller may comprise a motor which acts to actively advance (or enable) one or more units of product (to move) towards or through the aperture. The motor may drive a number of mechanical arrangements, although a rotary wheel which advances units of product towards aperture is preferred.

The one or more units of product will preferably be gravity fed to and through the aperture. If a gravity feed is utilised, then the dispenser may be configured to be stored or held upright so as to enable one or more units of product to be gravity fed to the aperture. The dispenser may be in the form of a cylindrical housing having a base and a top and where the base is larger than the top. In such configuration, the top is preferably substantially convex and optionally weighted so as to make the dispenser unstable unless it is stored in an upright position resting upon its base. This forces the individual to maintain the dispenser in the correct orientation for the gravity feed through the dispensing mechanism.

The dispenser may further comprise a communication arrangement for communicating to a remote server that a unit of product has been dispensed and/or the dispensing of a unit of product has been validated and/or the cap has been removed and/or reattached to the base after removal. The use of such a communication arrangement is particularly useful when logging and tracking consumption/compliance with a dosage regime.

In accordance with a further aspect of the present invention, there is provided a dispensing system comprising:
- a) a dispenser having a cavity for receiving at least one unit of product to be dispensed, a base having an aperture adapted to allow at least one unit of product to be dispensed when desired; and a dispensing control arrangement for controlling the dispensing of at least one unit of product through the aperture in the base in accordance with a dispensing protocol;
- b) an arrangement for setting or adapting the dispensing protocol; and optionally
- c) a communication arrangement for communicating to a remote server that a unit of product has been dispensed from the dispenser.

The dispensing system my further comprise a cap releasably attached to the base so as to cover the aperture in the base and capable of storing at least one unit of product after it has been dispensed.

Preferably, the dispensing system comprises a dispenser as described above, for use in controlling the dispensing of one or more units of a pharmaceutical, nutraceutical, nutritional or dietary supplements to an individual according to a pre-determined protocol and optionally relaying to a remote server that a unit has been dispensed.

In accordance with another aspect of the present invention, there is provided a product dispenser for dispensing and logging the consumption of a product contained therein comprising:
- a) a lid for a container comprising a cavity for receiving a plurality of product units to be dispensed, the lid having an aperture adapted to allow at least one unit of product to be dispensed when desired; and
- b) a counting arrangement for counting and communicating each unit of product which has been dispensed.

The counting and communicating arrangement may comprise a visual display showing the number of product units dispensed. The number of product units dispensed may be displayed on the visual display for a pre-determined time after each unit of product has been dispensed.

The at least one unit of product may be dispensed by a number of different ways. Preferably, it is by means of a mechanical action being performed on the lid. Such mechanical action may be twisting and/or pushing or pulling the lid or manipulating a feature on the lid such as depressing/pushing a button. Preferably, the lid may further comprise a child-safety feature to reduce the ability of a child from dispensing a unit of product. A number of child safety features will be already known to the skilled addressee.

The dispenser may be fitted to, or retrofitted, to a container having a plurality of product units located therein.

Preferably, a unique identifier is provided on or near to the counter. This enables data of the contents of the container and the identity of the individual to be easily correlated with the dosing frequency if the product is of a medicinal nature.

In accordance with yet a further embodiment of the present invention, there is provided a dispensing and logging system comprising:
- a) a container comprising a cavity for receiving a plurality of product units to be dispensed, and a lid having an aperture adapted to allow at least one unit of product to be dispensed when desired and a counting arrangement for counting and displaying each unit of product which has been dispensed; and
- b) a communication arrangement for interrogating and relaying the unit dispense count back to a remote server for logging purposes.

Preferably, the dispensing and logging system comprises a dispenser as herein above described, for use in controlling and logging the dispensing of how many units of a pharmaceutical, nutraceutical, nutritional or dietary supplement to an individual has been dispensed.

It will be apparent to the skilled addressee that the a number of compatible features will exist between the various aspects of the invention as described and therefore such compatible features will be interchangeable with one another.

DETAILED DESCRIPTION OF THE INVENTION

Embodiments of the present invention will now be described, by way of example only, with reference to the following examples and accompanying figures, in which.

Figures 1A, 1B:
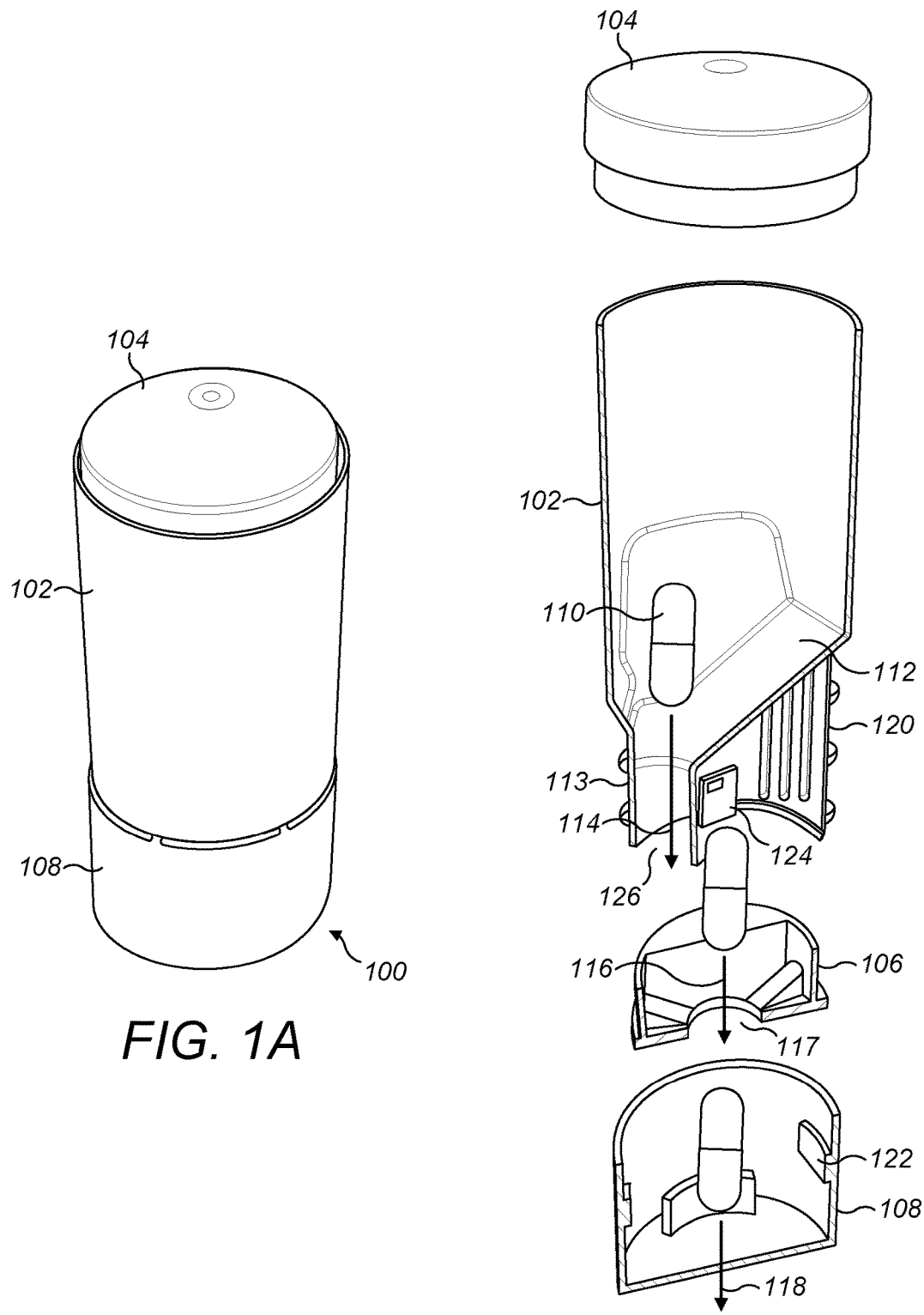
FIG. 1A is a perspective view of a dispensing container in accordance with the present invention.
FIG. 1B is an exploded cross-section perspective view of the dispensing container as shown in FIG. 1A.
Figure 1C:
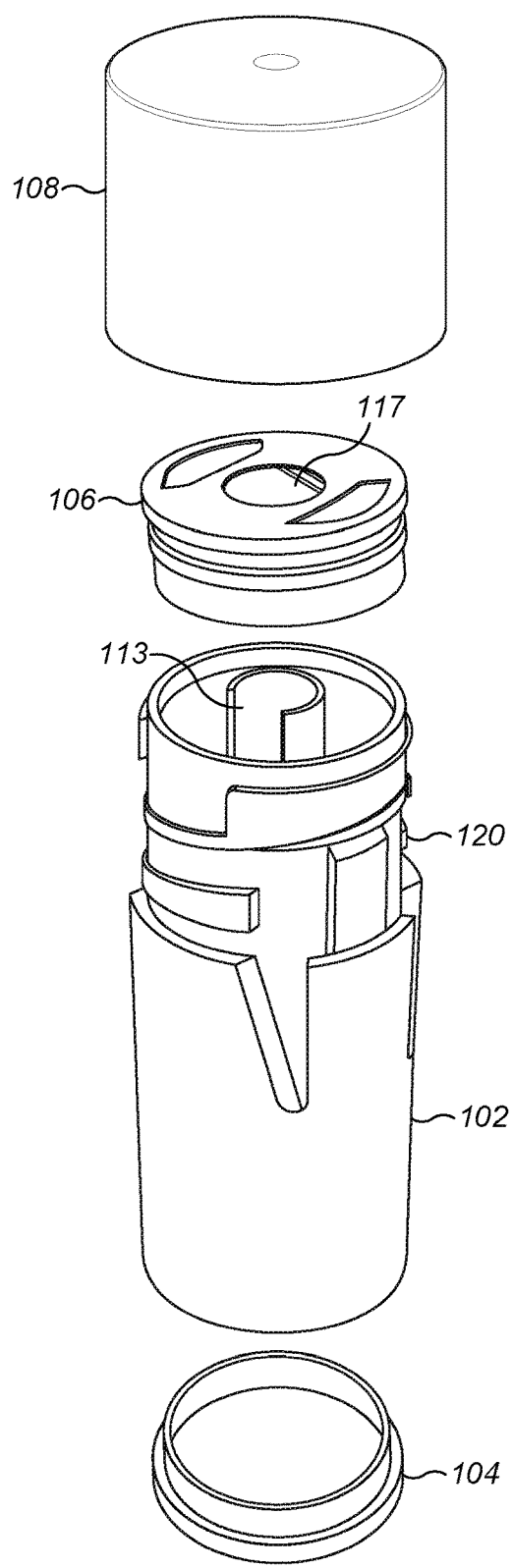
FIG. 1C is an exploded perspective view of the dispensing container as shown in FIG. 1A.

With reference to FIG. 1A-C, there is shown a dispensing container 100 in accordance with a first embodiment of the present invention. The dispensing container 100 comprises a cylindrical housing 102 having a round top at the top end of the cylindrical housing 102 and a dispensing base disc 106 located at the bottom end of the cylindrical housing 102. A removable base cap 108 covers the dispensing base disc 106 and is removably attached to the cylindrical housing 102 by means of projections 122 can be rotatably received around the threaded shank 120 of the cylindrical housing 102.

As shown in FIG. 1B, a pharmaceutical tablet 110 is located within the main body of the cylindrical housing and when placed in an upright position (as shown in FIG. 1B) the tablet 110 slides downwardly under gravity along the downwardly extending sloped inner wall 112 before passing down through the housing chute 113 and continues in a downwardly direction 114 and on to a surface of the dispensing base disc 106. The tablet can continue in a downwardly direction 116 through an aperture 117 in the dispensing disc 106 so that it ultimately falls into the removable base cap 108. When the removable base cap 108 is unscrewed, the cap can be moved away from the cylindrical housing 102 in a direction 118 so that the tablet can be easily removed by the user from the cap with their fingers and ingested by a patient. The cylindrical housing 102 also incorporated electronic circuitry 124 assessing user authentication and dispensing the tablet from the cylindrical housing through a dispensing flap 126 located at the exit of the cylindrical housing chute 113.

In use, each dispensing container 100 will be given a unique ID code which will be stored within the electronic circuitry 124 and the code will also be printed on the exterior of the cylindrical housing 102. The dispensing container 100 will be filled on a high speed (standard) pharmaceutical tablet bottling line and subsequently labelled and collated ready for shipping to the pharmacy. A pharmacist will dispense the bottle to the patient and the patient will then follow the instructions provided in order to permit access to the medication as and when required (as described with reference to later figures).

When a patient wishes to ingest a pharmaceutical tablet 110, they will first have to transmit a authentication code to the electronic circuitry 124 in order for the dispensing flap 126 to be opened and a tablet permitted to pass through the dispensing base disc 106 and into the removable cap 108. The user may use a number of means for providing the bottle with the authentication ID, but it is preferred that the code is provided wirelessly via a mobile phone which is configured only to provide the authentication ID after the identification of the user has been verified (either by means of facial recognition, fingerprint scanning, retina scan, pin code or password).

Figure 2:
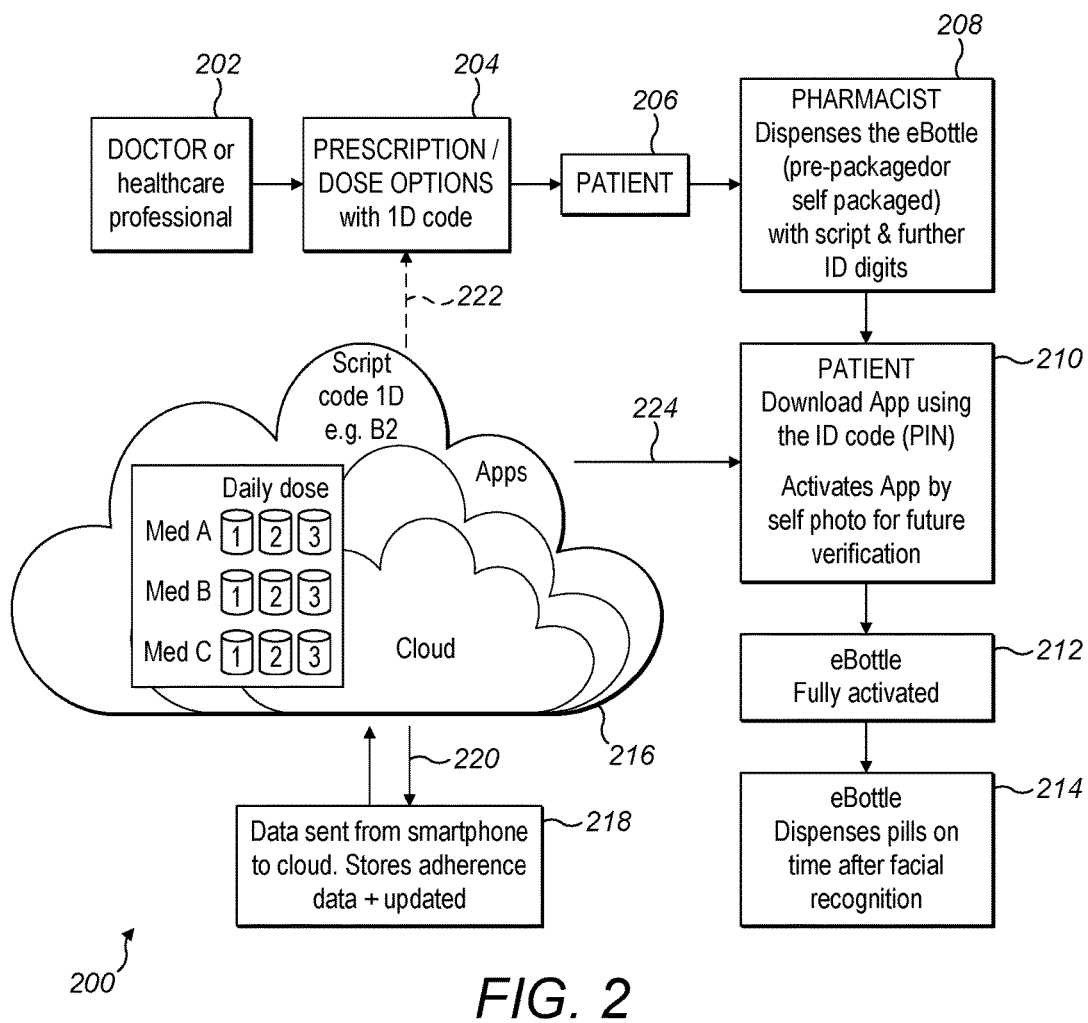
FIG. 2 is a schematic diagram for illustrating the steps undertaken by a doctor and patient in order to use the dispensing container of the present invention and their interaction with a remote database.

Turning to FIG. 2, there is shown schematically the system 200 of how a dispensing container as shown in FIGS. 1A-1C is configured to interact with a remote database. A doctor (or healthcare professional) 202 provides a prescription-dose regime 204 which includes a unique 1D code. The prescription 204 is given to the patient 206 who in turn passes it to a pharmacist 208 who provides the dispensing container which contains the required pharmaceutical tablets. The dispensing container is pre-packaged or self-packaged with a script and further ID digits. The patient then downloads a computer program (commonly referred to as an "app") to their telecommunication device using the ID code. In order to activate the computer program, the software prompts the use to take a photograph of themselves for future user verification. The dispensing container is then fully activated 212 and can dispense pharmaceutical tablets at the prescribed dose and time but only after the user has presented their face to the camera of the telecommunication device so as to provide a positive ID in the form of facial recognition 214. Data 218 is sent from and received by the telecommunication device and database 216 via any known communication route 220. The database 216 optionally provides the 1D codes during the prescription step 204 and may also house the software for the patient to download 224. If desired, the database 216 could be stored on a cloud based server or a hosted server with a secure network connection. It will be apparent to the skilled person, that during step 210, the patient need not necessarily download the software afresh, if the software already exists on their telecommunication device for a similar/repeat prescription or indeed a different prescription which is intended to be prescribed in the same manner.

Figure 3:
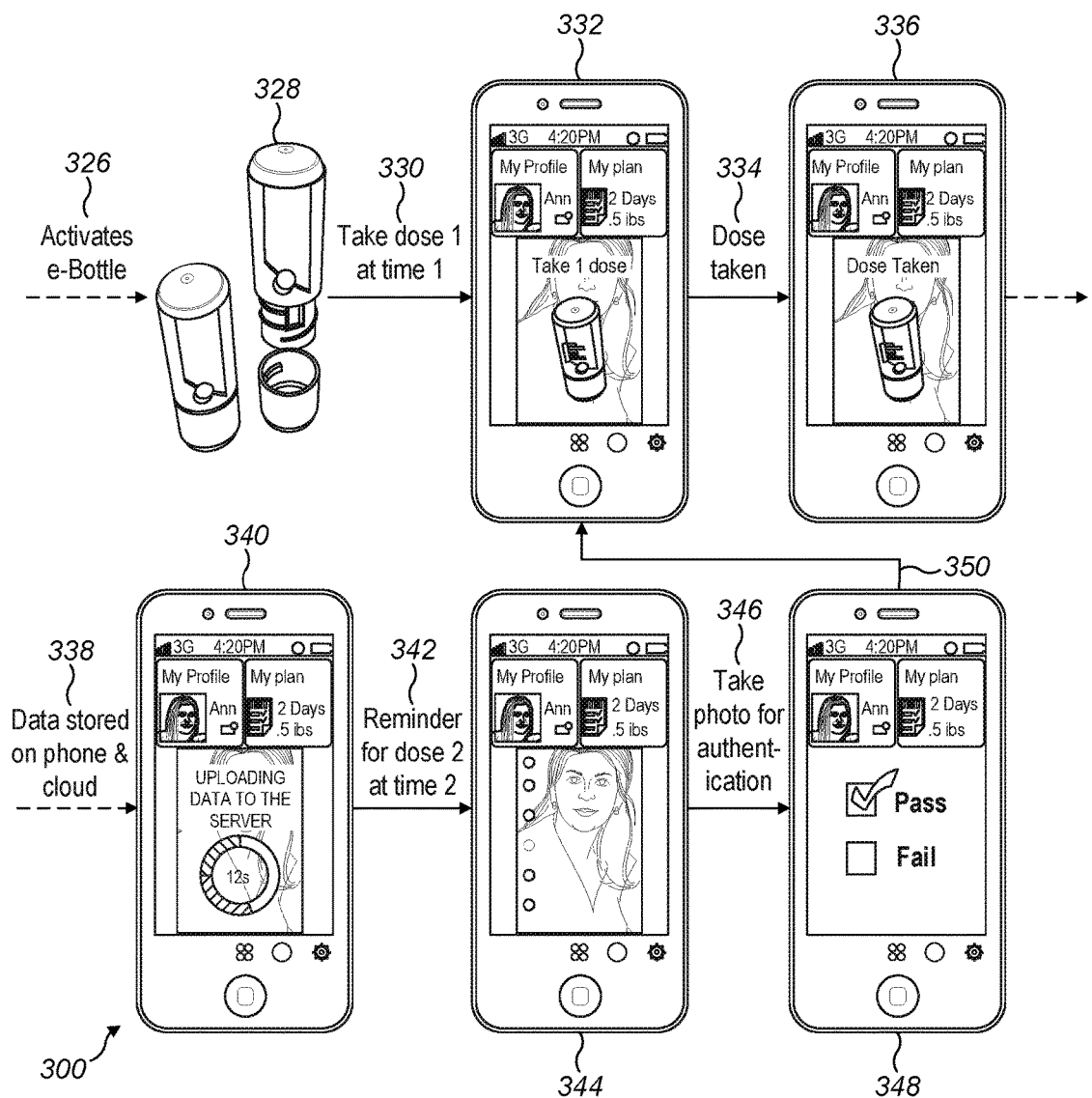
FIG. 3 is a schematic flow diagram of how a user may implement part of the invention using a mobile phone.

FIG. 3 shows the various software steps 300 which would take place when a patient downloads the software on to their telecommunication device in the format of a mobile phone so as to be able to access the medicine from the dispensing container. A patient would first download 302 the software onto their phone, during which a standard "download" screen 304 illustrating the time remaining for the software to be downloaded and installed on the phone will be presented to the user. The patient would then insert their ID code 310 which is linked to the visual recognition technology located either within the software on the phone or on a remote server. After the patient has inserted their ID code 310 on the "enter pin" 312 screen the patient is then prompted to take a photo 314 by means of a "take self photo" screen 316. A photo capture step 318 takes place where the patient 320 takes a photograph of their face using the integrated camera on the mobile phone and they then enter patient profile data 322 as requested on the patient profile page 324. By completing the patient profile in the software, this automatically activates 326 the dispensing container and enables the phone to start communicating directly with the microprocessor in the dispensing container 328. A single dose may be taken on time 330 as prompted by the software 332 and when a tablet has been taken from the container, the dose taken 334 is relayed back to the phone, and a "dose taken" 336 screen is presented on the phone. The data is then stored on the phone and also uploaded to the database 338 and confirmation that data has been uploaded to the server 340 is presented to the user screen. When a further dose is required, a reminder for a second dose at a second time period 342 is sent to the phone to alert the user via a reminder screen 344 and this prompts a photograph to be taken for authentication 346 and provided that the person who is photographed is recognised as the same picture in the original photo capture 318, the dispensing container is authorised to dispense a further dose and steps 332 to 348 repeated 350 as necessary.

Figure 4A:
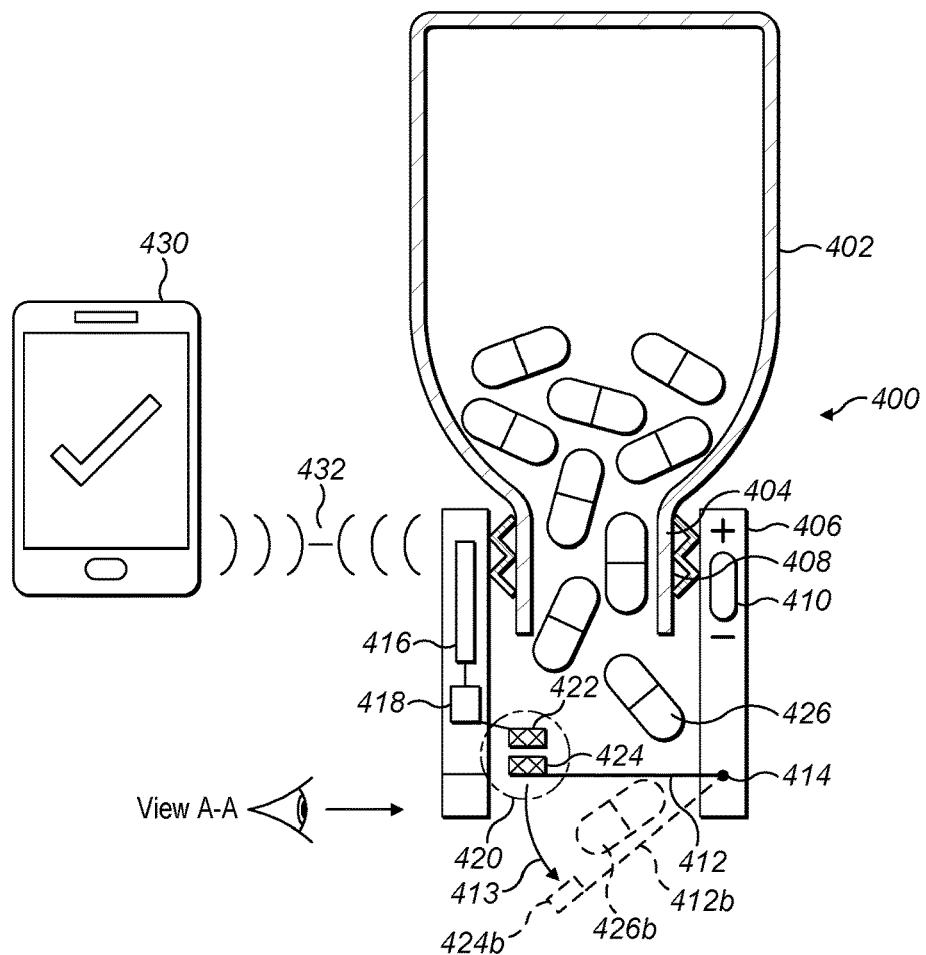
FIG. 4A is a cross-sectional diagram of an alternative embodiment of the dispensing container, where a standard tablet bottle is fitted with a cap capable of dispensing tablets in accordance with the present invention.
Figure 4B:
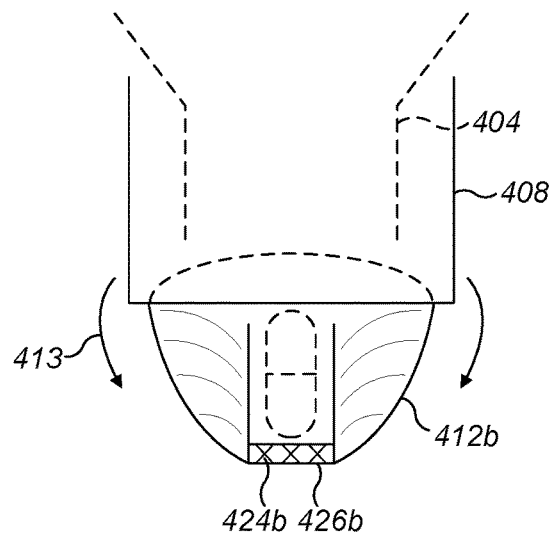
FIG. 4B is a side-view along view axis A-A (as shown in FIG. 4A) illustrating how the dispensing cap would present and dispose a tablet to a user.

With reference to FIG. 4, there is shown a bottle 400 with a dispensing cap in accordance with a second embodiment of the present invention. The bottle 402 is a standard pharmaceutical tablet bottle which has a neck 404 with a threaded shank 408 for sealing with a sealing cap. A dispensing cap having a cap housing 406 has been rotated received onto the threaded of the neck of the bottle 404 in a secure matter. It is desirable for the cap housing 406 to be permanently affixed around the neck of the bottle 404 such that it cannot be removed.

The cap housing 406 houses a battery 410 for powering the electronic circuitry within the cap housing 406. An access flap 412 is shown in a closed configuration at the base of the cap housing. The access flap can move to open configuration (shown in hatched lines 412b). The flap 412, 412b pivots about a hinge 414 and permits the flap to move in an arcuate direction 413. The cap housing 406 also incorporates an aerial 416 for communicating with an external device such as a mobile phone. The aerial 416 is operably connected to a microprocessor 418 which in turn is connected to a locking mechanism 420 for controlling the movement of the access flap 412. The locking mechanism 420 comprises an electromagnet 422 which can abut a strip of ferrous material 424 located on the interior surface of the access flap 412. Within the bottle 402 are a number of pharmaceutical tablets 426 which can be received within a channel of the access flat 412 so that a single tablet can be dispensed during one access flap opening. A schematic telecommunication device 430 is shown which is in wireless communication 432 with the microprocessor 418 via the aerial 416.

As the bottle 402 may be a standard bottle, the cap 406 could be retrofitted to the bottle, or simply formed or affixed onto the bottle during the normal packaging process. When a patient wishes to ingest a pharmaceutical tablet 426, they use the system 200 and take the necessary steps on their phone 300 to effect a positive ID authentication from the telecommunication device 430 which is sent wirelessly 432 to the aerial 416 of the cap housing 406. The microprocessor 418, upon receipt of an authentication code disengages the electromagnetic locking arrangement 422 so as to release the access flap 412 so that it moves to an open configuration 412b and a single pharmaceutical tablet 426b is presented to the user for consumption. The user then pushes the access flap 412b back towards the cap housing 406 and the microprocessor 418 automatically activates the electromagnet 422 which secures the access flap to the strip of ferrous material 424. Different locking mechanisms may also be deployed.

Figure 5:
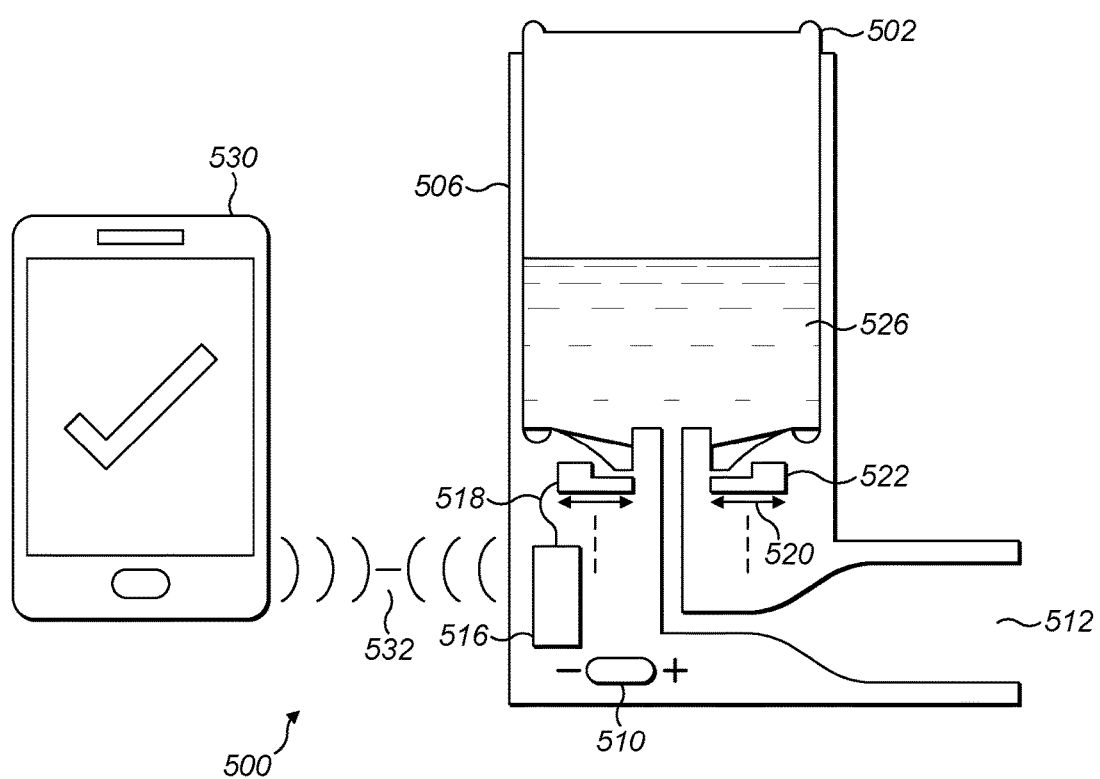
FIG. 5 shows a yet further embodiment of the dispensing container in accordance with the present invention, where the container contains a liquid and the housing is capable of dispensing a spray to a patient.

FIG. 5 shows a bottle with aerosol dispenser in accordance with a third embodiment of the present invention. In this embodiment, an aerosol can 502 is received within a dispenser housing 506. The dispenser housing 506 also contains a battery 510 which powers a microprocessor 518 and the locking mechanism 522. A liquid pharmaceutical medicine 526 is contained within the aerosol can and is capable of being in fluid communication with the liquid aerosol dispensing nozzle 512 when the locking mechanism 522 has been disengaged. In common with the bottle with dispensing cap in accordance with the second embodiment shown in FIG. 4, the aerosol dispenser also communicates with a telecommunication device 530 via an aerial 516 using a wireless connection 532. Again, when the telecommunication device 530 transmits a user authentication signal to the microprocessor 518 via the aerial 516, it disengages the locking mechanism 522 for a single metered dose of the liquid pharmaceutical medicine 526 via the liquid aerosol dispensing nozzle 512. After the single does has been dispensed, the locking mechanism 522 engages so as to prevent any further doses being dispensed until such time that an authentication code is again provided by the telecommunication device 530.

Figure 6:
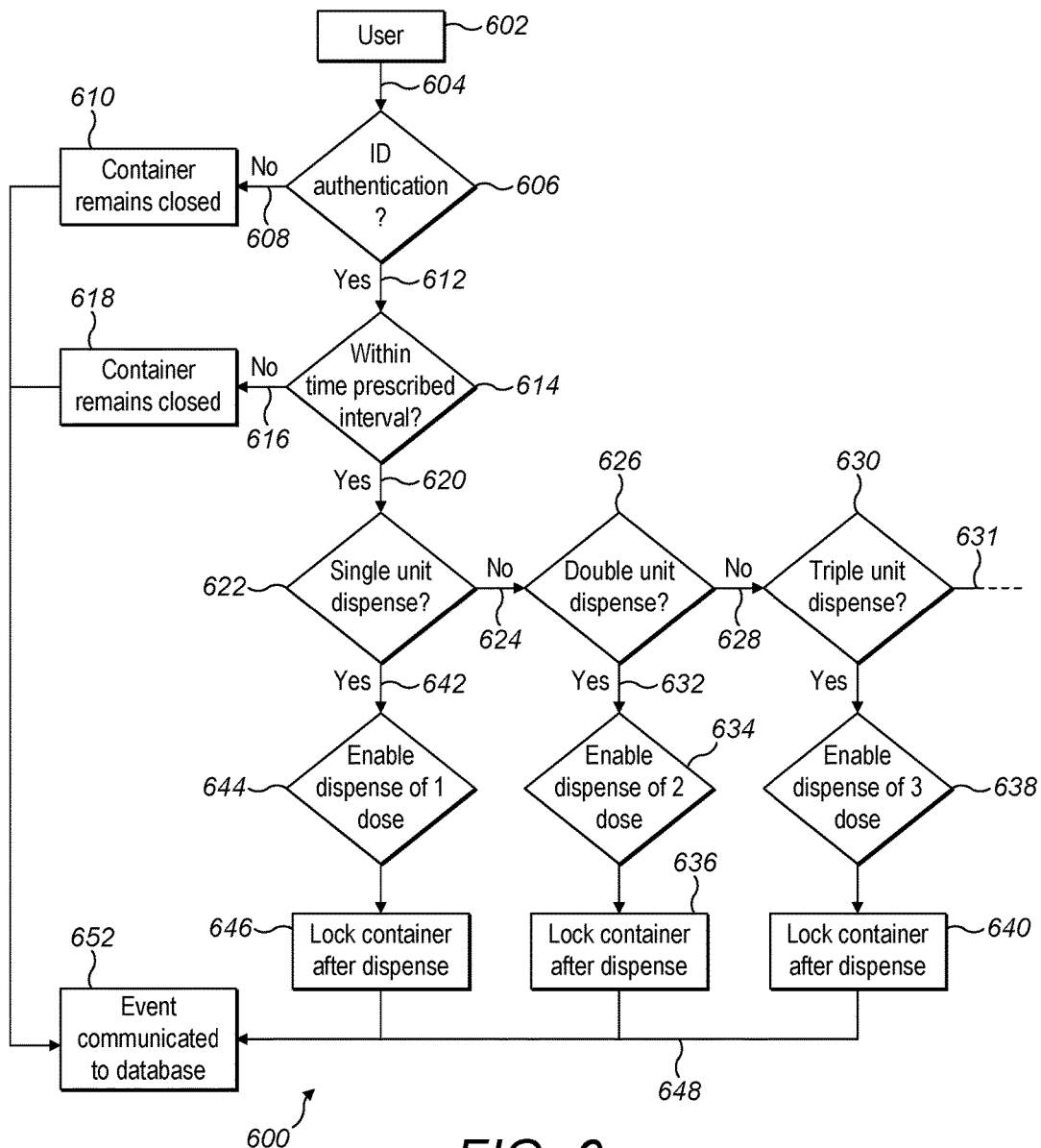
FIG. 6 is a schematic flow-diagram illustrating the steps a patient would make during the operation of the dispensing container of the present invention.

With reference to FIG. 6, there is shown a schematic flow chart 600 of the necessary steps a user may take in order to obtain a pharmaceutical dose from a dispensing container in accordance with embodiments of the present invention. The user 602 is required 604 to provide ID authentication 606 to the container. If no ID authentication is provided 608, the container remains closed 610. If a ID authentication 606 is provided 612, then is the request for a further pharmaceutical dose within the prescribed time interval 614? If the request is not within the prescribed time frame 616, then the container remains closed. If the request is within the prescribed time interval 620, the system then needs to establish whether a single dose 622 is required. If only a single dose is required 642 then the container is enabled to dispense one dose 644 after which, the container is locked 646 after dispensing the dose. If more than one single dose is required 624 is a double dose required 626? If yes 632, then the container is enabled to dispense 2 doses 634 before the container is locked 636. If more than 2 doses are required 628, then if a triple dose is required 630, the container is enabled to dispense 3 doses 638, after which the container is locked 640. The process continues 631 depending on the number of doses required. If a single, double or triple (646, 636, 640) has been dispensed then the event is communicated 648 to a central database 652. If unauthorised requests or out of time interval requests have been received (610, 618), then this information is also relayed 650 to the central database 652.

Figure 7A:
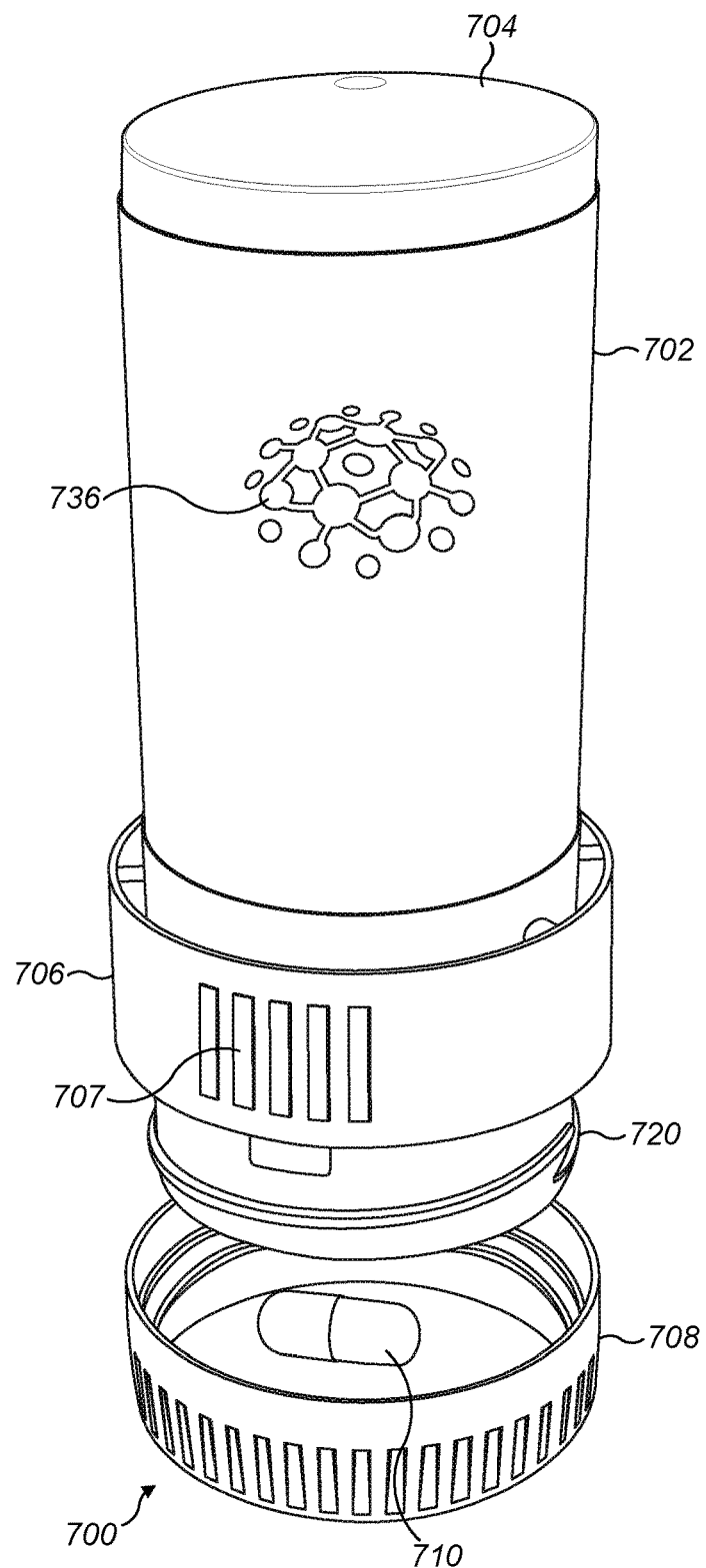
FIG. 7A is a perspective view of a dispensing container in accordance with a further aspect of the present invention, where the end cap has been removed.
Figure 7B:
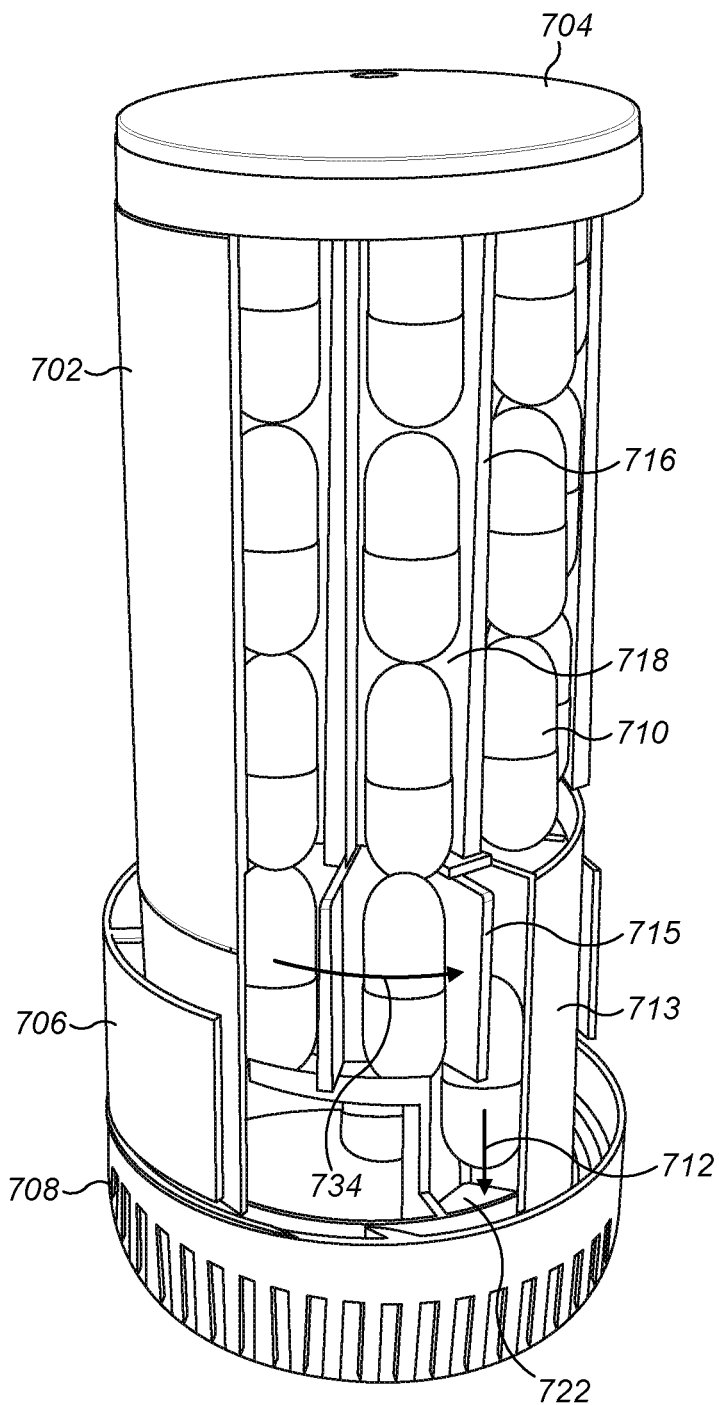
FIG. 7B is a cross-sectional view of the dispenser shown in FIG. 7A, where the end cap has not been removed.
Figure 7C:
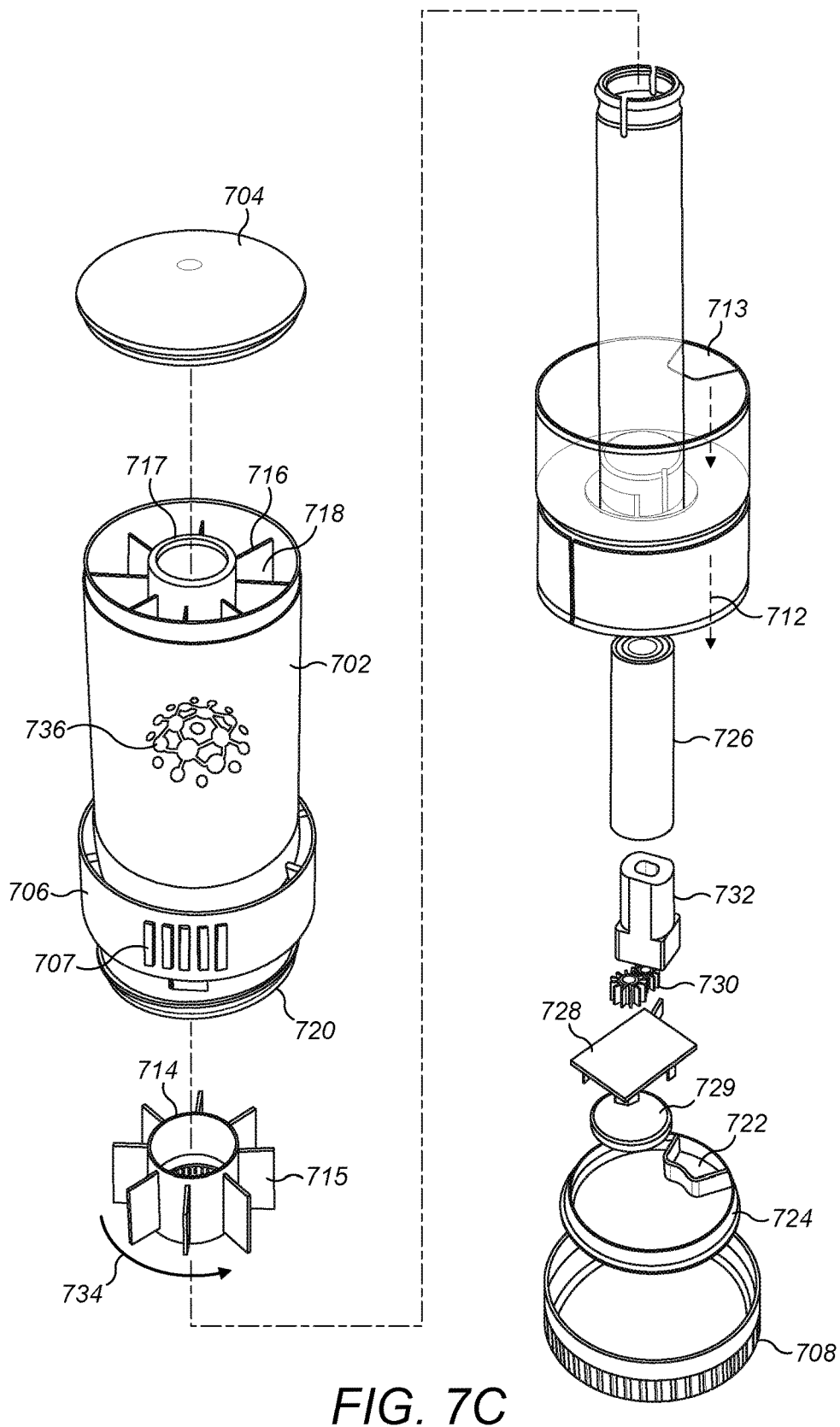
FIG. 7C is an exploded perspective view of the component parts of the dispensing container shown in FIGS. 7A and 7B.

FIG. 7A illustrates a dispensing container which is similar in its mode of action to a dispensing container as described with reference to (and as illustrated in) FIG. 1. With reference to FIG. 7A-7C, the dispensing container 700 of this embodiment has an outer cylindrical body 702 which is closed at the top by means of a weighted top cap 704. Extending circumferentially around the base of the outer cylindrical body 702 is an outer rim 706 having a number of longitudinally extending projections 707 forming easy to grip features on the rim. Directly under the outer rim 706 is a threaded shank 720 around which is secured a rotatably removable base cap 708. In FIG. 7A, the base cap 708 is shown in a position away from the outer cylindrical body 702 and contains a pharmaceutical tablet 710 which has been dispensed. The base cap 708 has a flat lower surface (not shown) which is used to support the container in an upright fashion when resting on a flat surface. The direction of the flow of the pharmaceutical tablet 710 out of the cylindrical body 702 is illustrated by the arrow denoted 712 which shows that the tablet 710 is dispensed into the removable base cap 708 via a chute 713 located towards the bottom of the cylindrical body 702.

Towards the base of the cylindrical body 702 is a rotatable star 714 which is in the configuration of a small cylinder which is rotatable along the longitudinal axis of the cylindrical body 702 and from which 8 fins 715 extend in a radial fashion. The spacing of the radial fins 715 corresponds to longer fins 716 located on a static star 717 located above the rotatable star 714 which is connected to a ratchet mechanism (not shown). The longer fins 716 form channels within the star 718 and enable end-to-end vertical stacking of pharmaceutical tablets 710.

The chute 713 abuts a lower disc 724 located beneath the rotatable star 714. The lower disc 724 is provided with an aperture 722 for allowing the pharmaceutical tablet 710 to be dispensed into the removable base cap 708 when desired.

In a central portion of the dispensing container 700, there is provided a drive mechanism, power source and communication arrangement. An AA battery 726 provides power to a motor 732 which is adapted to rotate the rotatable star 714 via a gearing mechanism 730. A microprocessor 728 is provided and attached to a communication arrangement (such as an antenna and Bluetooth® communication software).

In use, the dispensing device 700 operates in a very similar manner as to the dispensing device illustrated in FIG. 1. When assembled, the dispensing container 700 forces the user to keep the device in an upright configuration as the top cap 704 is weighted such that if the container is not held or placed on a surface in a vertical manner, the container will be unstable and topple over. This feature is important as it forces the user to keep the dispensing container in its upright configuration which permits the pharmaceutical tablet 710 to be gravity fed into the rotatable star 714 and ultimately into the removable base cap 708. The top cap 704 also permits the dispensing container to be easily filled at a production facility or a pharmacy.

Initially, pharmaceutical tablets 710 are stacked end-to-end within the static star channels 718 and the stack extends into the space formed between the fins 715 of the rotatable star 714. When the dispensing container is activated, the rotatable star 714 is powered by the battery 726 drives the motor 732 which in turn activates the gearing mechanism 730 and very rotates the ratchet mechanism of the rotatable star 714 in a direction 734. When the tablet 710 is rotated to a position adjacent to the chute 713, the pharmaceutical tablet is able to drop by gravity through the aperture 722 in the lower disc 724 and into the removable base cap 708. A dispensing sensor (not shown) may also be provided for validation purposes which detects and confirms the dispensation of a tablet 710. A dispensing sensor may be a micro-switch arrangement which detects the physical passage of the tablet or a light sensor which can detect the optical passage of the tablet. The dispensing sensor may be located adjacent to or within the chute 713. When the user is ready to take their medicine, they simply unscrew the removable base cap 708 and remove the pharmaceutical tablet 710 and then consume it for their treatment. The rotatable star 714 can be pre-set to rotate at a particular speed so that one or more tablets 710 are dispensed at pre-determined time points. The microprocessor 728 can not only control the speed of the rotation of the rotatable star 714 through the gearing arrangement 730, but may also communicate the removal of the base cap 708 and/or the dispensing of a tablet 710 through the aperture 722 (which may include validation of the dispensing by utilising the dispensing sensor) to a remote server for compliance monitoring. Should dispensing action not be validated by the dispensing sensor, then an error signal may be sent to the remote server for appropriate action. Alternatively, the dispensing container 700 could be used in conjunction with an authentication protocol so that the rotatable star 714 only rotates to a position to allow a pharmaceutical tablet 710 to be dispensed through the chute 713 and aperture 712 upon receipt of an authorisation signal. The dispensing container 700 is particularly suited for the timed dispensation of drug rehabilitation treatments such as methadone, as the dispensing container cannot be opened by the user and will only dispense tablets at prescribed time points. Of course, an override system may also be provided to enable dispensation of tables in emergencies and/or malfunction of the software or mechanism.

The dispensing container 700 may be used in conjunction with the system 200 (shown in (and described with reference to) FIG. 2) for configuring a dispensing container with a remote database, in addition to using the software steps 300 (shown in (and described with reference to) FIG. 3) and lastly the necessary steps a user may take in order to obtain a pharmaceutical dose from a dispensing container using the steps 600 (shown in (and described with reference to) FIG. 6).

As a further modification to the dispensing container 700, or as an emergency back-up, the advancement of the tablet 710 through the chute 713 may be by the user twisting the collar 706 which would be operably connected to the rotatable star 714 in such a manner that the twisting action would rotate the fins 715 enough so that a tablet could be dispensed. There may be an additional mechanism included which prevents the rotation of the collar (and therefore dispensation of the tablet) unless the prescribed time had lapsed or a correct authentication code had been received.

Figure 8A:
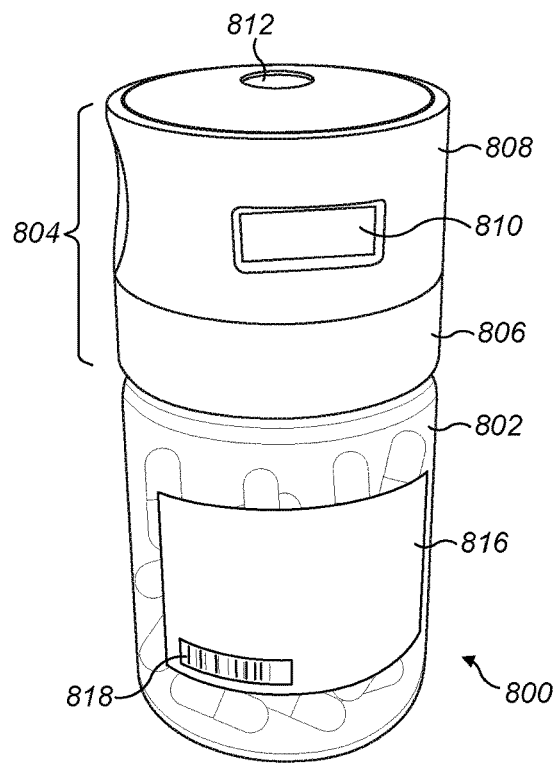
FIG. 8A is a perspective view of a yet further embodiment of the present invention.

With reference to FIGS. 8A-8A, there is a yet further dispensing container 800 shown related to the present invention. The dispensing container 800 is formed of a standard tablet bottle 802, upon which is attached a dispensing lid 804. The dispensing lid 804 is formed of a bottle sealing rim 806 and a dispensing portion 808. The dispensing portion 808 has a dispensing counter 810 and an aperture 812 through which pharmaceutical tablets 814 can be dispensed.

The tablet bottle 802 has a label 816 having a unique barcode 818 included thereon.

The bottle sealing rim 806 is statically received on the tablet bottle 802, but permits the dispensing portion 808 to rotate in a clockwise direction 820 by 90° so as to enable a pharmaceutical tablet 814 to be dispensed through the aperture 812 in the direction indicated by the arrow 822. The dispensing portion 808 is spring loaded and after dispensing a tablet, it counter rotates in an anti-clockwise direction by 90° and therefore assumes its original position ready for the next tablet to be dispensed.

In use, the tablet bottle 802 will be filled with pharmaceutical tablets 814 which may contain a medicine such as a severe pain relief formulation. When the user wishes to take a medicine, they simply rotate the dispensing portion 808 relative to the bottle 802 and a pharmaceutical tablet 814 is dispensed through the aperture 812 in the direction 822. As the tablet 814 passes through the dispensing portion 808 or the aperture 812, the dispensing counter 810 is advanced by an additional number, thus indicating the total number of tablets dispensed. The dispensing counter 810 may be analogue or digital and may be in the form of a LED or LCD display.

The dispensing container 800 may be used simply to allow an individual track the number of doses taken from the bottle or the container could be utilised for more active monitoring of the dispensing of the tablets from the bottle. In the latter, an image capture device 824 (such as a camera on a smartphone) may be used to take an image of the whole of the dispensing container 800 or a first 826 and/or second 828 focus area. The image capture device 824 may be further refined to take two images or to focus on two areas of the bottle, namely the dispensing counter 810 and the label 816 which contains a unique barcode 818. Alternatively or additionally, a barcode 826 may be attached near to the dispensing counter 810 so that the image capture device need only be focused towards the first focus area thus removing the need to receive an image from the second focus area 828.

The dispensing container 800 could be used in a number of ways, although it is envisaged that a smartphone (not shown) is used to relay when a dose from the bottle has been taken by sending data from the display counter 810 and unique barcode 818 (or 826) to a remote server for dose monitoring and/or reordering purposes.

Figure 8B:
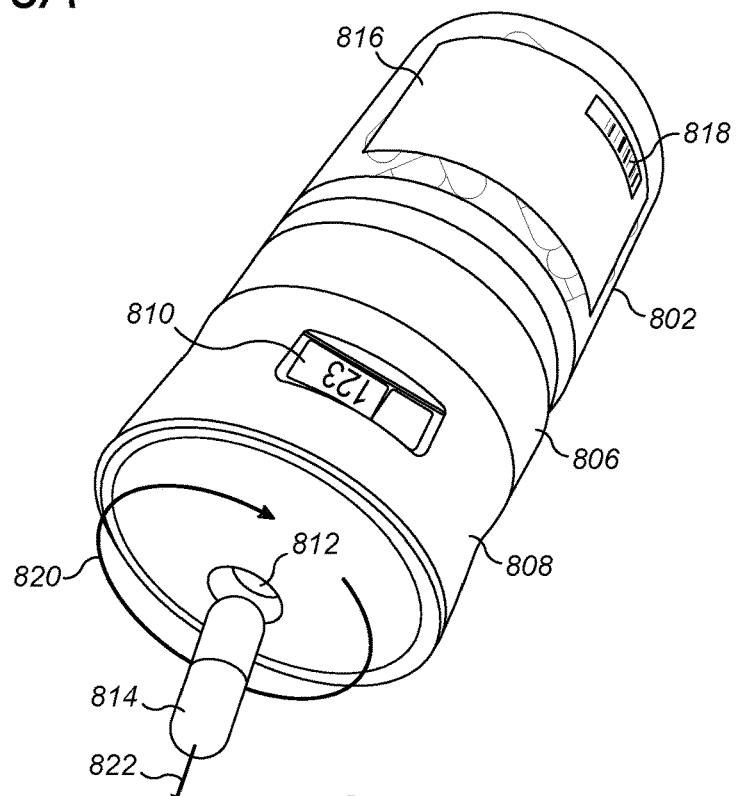
FIG. 8B is a further perspective view of the dispensing container as shown in FIG. 8A.
Figure 8C:
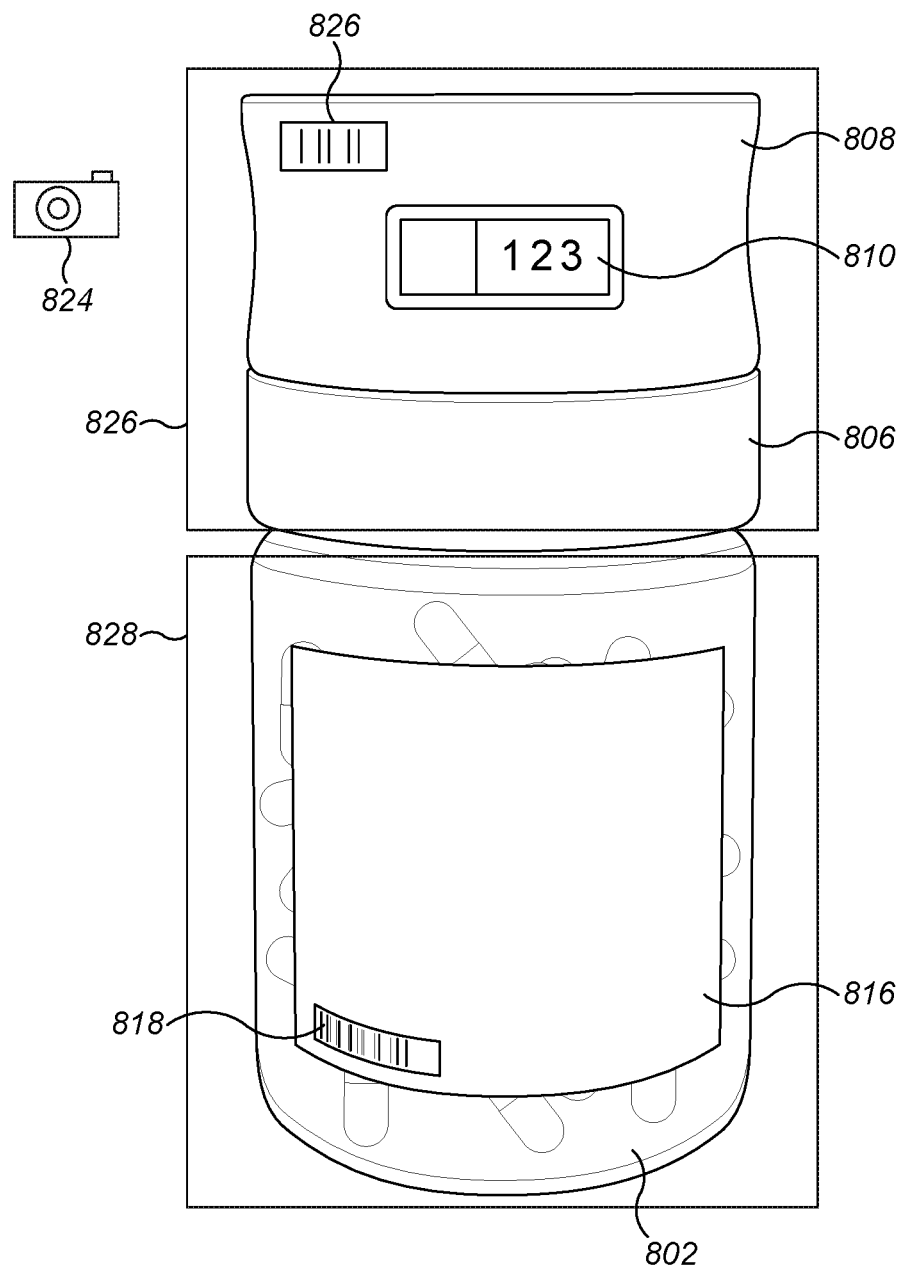
FIG. 8C is a front view of the dispensing container shown in FIG. 8B, showing outlined boxes which may be photographed/analysed by an imaging device.
Figure 9:
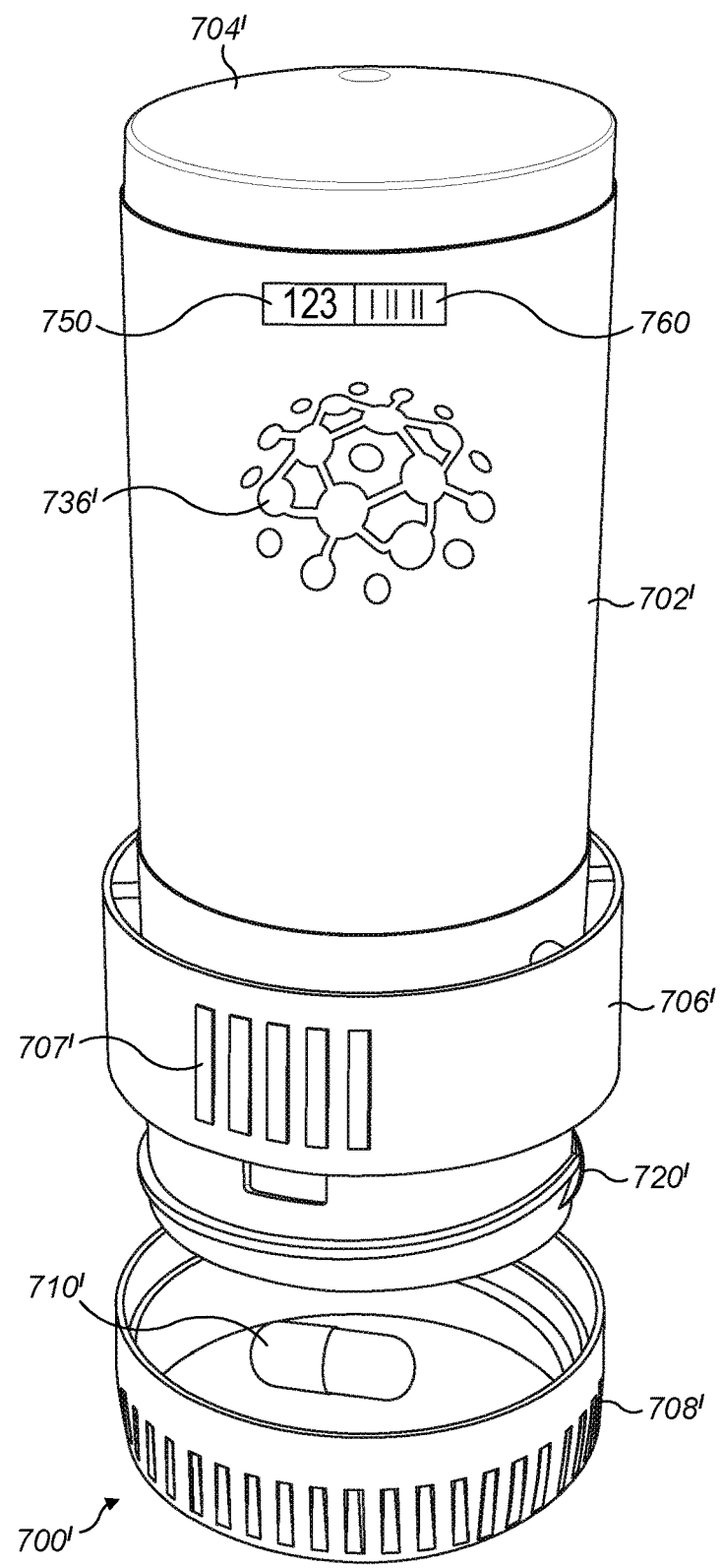
FIG. 9 shows a similar dispensing container as shown in FIGS. 7A-7C but differs in the fact that it contains a tablet counter and bar code.

Lastly, FIG. 9 shows a similar dispensing container as shown in FIGS. 7A-7C. In view of this similar features have been denoted by the same reference numeral prime ('). The dispensing container 700' also includes a counter 750 which counts the numbers of tablets dispensed in a similar manner to the counter 810 and also a unique barcode 760. The counter 750 may also be able to log and display additional information such as the time the last table was dispensed, how many tablets have been dispensed so far and how many tablets remain in the container. By including the counter, the dispensing container 700' can be used (either additionally or alternatively) in a similar way as shown and described with reference to FIGS. 8A-C, where a imaging device (such as a smart phone) is used to track and relay information about the frequency and timing of tablet dispensation. Furthermore, the counter could also include an alert function such as flashing or audible alarm in order to remind an individual to take another dose.

It will of course be apparent, that the devices and system as described with reference the aforementioned embodiments can be used not only to prevent unauthorised access to the medicines within the containers (for example to reduce the likelihood of children gaining access to pharmaceutical products) but they can also be used to monitor patient compliance and ensure correct dosage regimes are followed in accordance with the recommended guidelines. By utilising a telecommunication device such as a "smartphone", software embedded in the phone or a computer program operating on the phone can automatically remind patients to take the medicines at the correct timings and the software can also include features to take account of patients travelling between time zones, whilst maintaining correct dosage regimes which are often difficult for travellers etc.

The configuration of the containers and dispensing mechanisms described above can of course be interchanged depending upon the precise application and therefore the foregoing embodiments are not intended to limit the scope of the protection afforded by the claims, but rather to describe examples of how the invention may be put into practice.

The invention claimed is:

1. A dispensing container comprising:
   a) a cavity for receiving at least one unit of product to be dispensed;
   b) a base having an aperture adapted to allow at least one unit of product to be dispensed when desired; and
   c) a controller for controlling the dispensing of at least one unit of product through the aperture in the base in accordance with a dispensing protocol, wherein the dispensing protocol comprises receiving a user authentication signal from a remote device and receiving or assessing whether the user is within the prescribed vicinity of the container, the user authentication signal indicating that an authorised user has been successfully identified by the remote device and wherein the controller only permits the dispensing of at least one unit of product upon receiving the user authentication signal from the remote device and upon determination that the user is within the prescribed vicinity of the container.

2. The container as claimed in claim 1, wherein the container further comprises:
   a cap releasably attached to the container so as to cover the aperture of the base.

3. The container as claimed in claim 2, wherein the cap comprises a child-safety feature to reduce the ability of a child from dispensing a unit of product.

4. The container of either claim 2, wherein the cap is capable of storing at least one unit of product after it has been dispensed.

5. The container of claim 1, wherein the base is retro-fitted to the opening of an existing container.

6. The container of claim 5, wherein the existing container comprises a medical bottle.

7. The container as claimed in claim 1, wherein user authentication signal is provided by successfully identifying an authorised user by using one of the following: facial recognition, finger prints, retina scan, PIN code or password.

8. The container as claimed in claim 7, wherein the user authentication signal is provided upon verifying the user against identification data located on a remote server.

9. The container as claimed in claim 1, wherein the remote device comprises a mobile phone.

10. The container as claimed in claim 1, wherein the controller comprises a micro-switch or ratchet arrangement which controls the dispensing of one or more units of product through the aperture.

11. The container as claimed claim 1, wherein the controller comprises a motor which acts to advance one or more units of product towards or through the aperture.

12. The container as claimed claim 11, wherein the motor drives a rotary wheel which advances units of product towards aperture.

13. The container as claimed in any one of claim 1, wherein the one or more units of product are gravity fed to and through the aperture.

14. The container as claimed in claim 13, wherein the dispenser is configured to be stored or held in a position so as to enable one or more unit of product to be gravity fed to the aperture.

15. The container as claimed in claim 1, wherein the product is in the form of a tablet or capsule.

16. The container as claimed in claim 1, wherein the product comprises a pharmaceutical, nutraceutical, nutritional or dietary supplement.

17. The container as claimed in claim 1, wherein the dispenser further comprises a communication arrangement for communicating to a remote server that a unit of product has been dispensed and/or the dispensing of a unit of product has been validated.

18. A kit of parts for producing a dispensing container comprising:
   a) a container having a cavity for receiving at least one unit of product to be dispensed;
   b) a base for the container having an aperture adapted to allow at least one unit of product to be dispensed when desired; and
   c) a controller for controlling the dispensing of at least one unit of product through the aperture in the base in accordance with a dispensing protocol, wherein the dispensing protocol comprises receiving a user authentication signal from a remote device and receiving or assessing whether the user is within the prescribed vicinity of the container, the user authentication signal indicating that an authorised user has been successfully identified by the remote device and wherein the controller only permits the dispensing of at least one unit of product upon receiving the user authentication signal from the remote device and upon determination that the user is within the prescribed vicinity of the container.

19. The kit of parts as claimed in claim 18, wherein the kit further comprises:
   d) a cap releasably attached to the container so as to cover the aperture of the base.

20. The kit of parts as claimed in claim 18, wherein the product is a tablet or capsule.

* * * * *